United States Patent
Khajavi et al.

(10) Patent No.: US 11,197,940 B2
(45) Date of Patent: Dec. 14, 2021

(54) MULTI-FUNCTIONAL SANITIZATION APPARATUS AND RELATED METHODS

(71) Applicant: STARTBOX, LLC, Atlanta, GA (US)

(72) Inventors: Kaveh Khajavi, Atlanta, GA (US); David E. Lane, Falkville, AL (US)

(73) Assignee: STARTBOX, LLC, Atlanta, GA (US)

( * ) Notice: Subject to any disclaimer, the term of this patent is extended or adjusted under 35 U.S.C. 154(b) by 0 days.

(21) Appl. No.: 15/778,545

(22) PCT Filed: Nov. 23, 2016

(86) PCT No.: PCT/US2016/063648
§ 371 (c)(1),
(2) Date: May 23, 2018

(87) PCT Pub. No.: WO2017/091756
PCT Pub. Date: Jun. 1, 2017

(65) Prior Publication Data
US 2018/0280554 A1   Oct. 4, 2018

Related U.S. Application Data

(60) Provisional application No. 62/258,835, filed on Nov. 23, 2015.

(51) Int. Cl.
*A61L 2/10* (2006.01)
*A61L 2/24* (2006.01)

(52) U.S. Cl.
CPC .............. *A61L 2/10* (2013.01); *A61L 2/24* (2013.01); *A61L 2202/122* (2013.01); *A61L 2202/14* (2013.01); *A61L 2202/181* (2013.01)

(58) Field of Classification Search
CPC .......... A61L 2/10; A61L 2/24; A61L 2202/14; A61L 2202/122; A61L 2202/181
See application file for complete search history.

(56) References Cited

U.S. PATENT DOCUMENTS

2009/0148358 A1*  6/2009  Wind ................. A61L 2/10
                                              422/186.3
2009/0265990 A1* 10/2009  Stratmann ........... A47K 5/12
                                              49/31
(Continued)

FOREIGN PATENT DOCUMENTS

KR   20030033475 A    5/2003
KR   20030083662 A   10/2003
(Continued)

OTHER PUBLICATIONS

Shrink Film Information (https://uspackagingandwrapping.com/shrink-film-101.html) (Year: 0).*
(Continued)

*Primary Examiner* — Sean E Conley
*Assistant Examiner* — Brendan A Hensel
(74) *Attorney, Agent, or Firm* — Meunier Carlin & Curfman LLC

(57) ABSTRACT

The present invention relates to a method and apparatus for preventing bacterial cross-contamination between a user's personal item and a bacterially sensitive environment. More particularly, the present invention is directed to a method and apparatus for sanitizing a user's hands and cell phone prior to the user entering into a sterile operating room, thereby minimizing the introduction of contaminants via the cell phone.

11 Claims, 5 Drawing Sheets

(56) References Cited

U.S. PATENT DOCUMENTS

| | | | |
|---|---|---|---|
| 2010/0044582 A1 | 2/2010 | Cooper et al. | |
| 2012/0248332 A1* | 10/2012 | Kreitenberg | A61L 2/10 |
| | | | 250/455.11 |
| 2014/0245866 A1* | 9/2014 | Hadlock | A61L 2/10 |
| | | | 81/9.2 |
| 2014/0322070 A1* | 10/2014 | Thomas | A61L 2/00 |
| | | | 422/1 |

FOREIGN PATENT DOCUMENTS

| | | | | |
|---|---|---|---|---|
| KR | 20130011874 A | 1/2013 | | |
| WO | 2013/082284 A1 | 6/2013 | | |
| WO | WO-2013/082284 | * 6/2013 | ............... | A61L 2/10 |
| WO | WO-2014/134299 | * 4/2014 | ............... | A61L 9/20 |
| WO | 2014/134299 A1 | 9/2014 | | |

OTHER PUBLICATIONS

International Search Report and Written Opinion issued in related International Application No. PCT/US2016/063648 dated May 3, 2017.

* cited by examiner

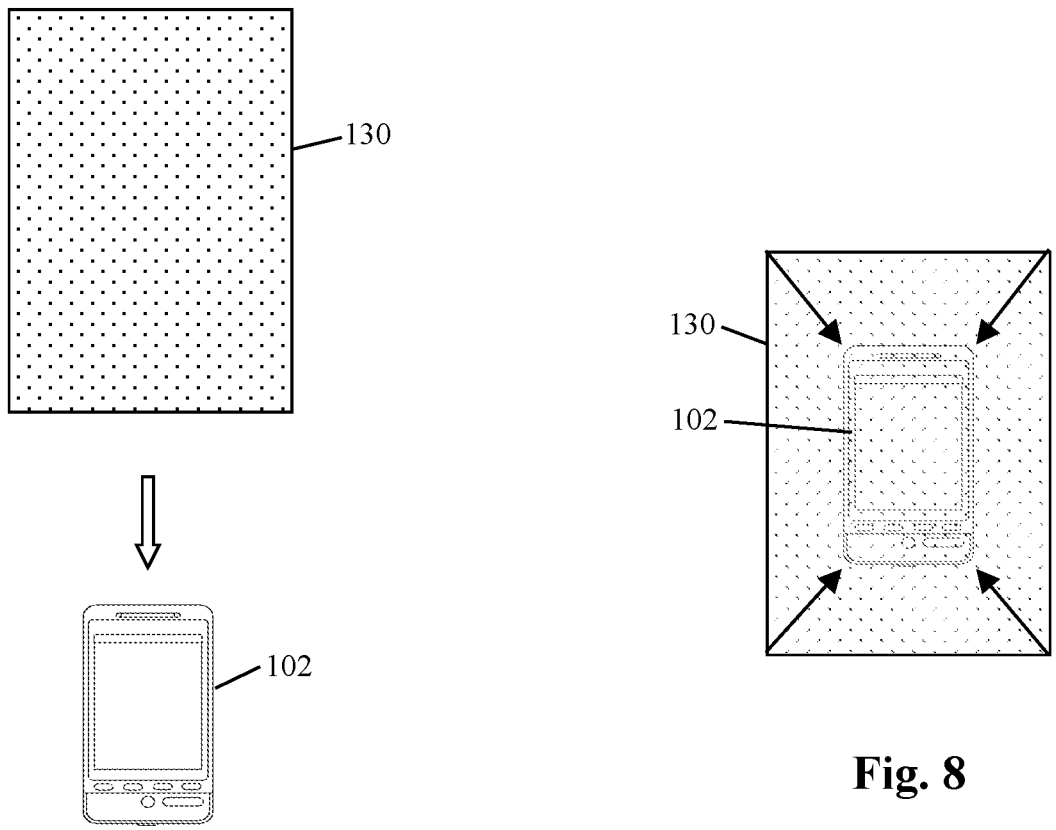
Fig. 7
Fig. 8
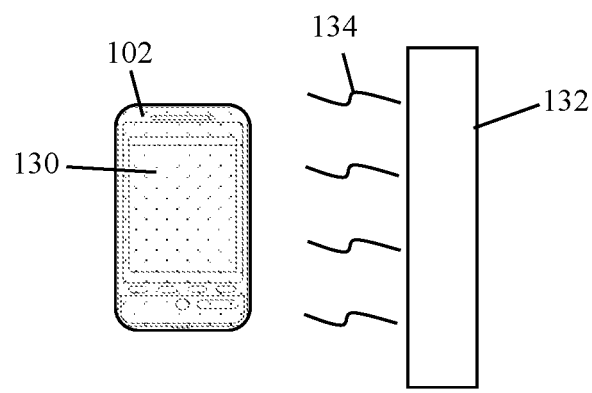
Fig. 9

MULTI-FUNCTIONAL SANITIZATION APPARATUS AND RELATED METHODS

CROSS-REFERENCES TO RELATED APPLICATIONS

The present application is a national stage application filed under 35 U.S.C. 0371 of PCT/US2016/063648, filed Nov. 23, 2016, which is a non-provisional application claiming the benefit of priority from commonly owned U.S. Provisional Application Ser. No. 62/258,835 filed on Nov. 23, 2015 and entitled "METHOD AND DEVICE FOR REDUCING THE RISK OF NON-STERILE, NON-SURGICAL ITEMS BROUGHT INTO A SURGICAL SETTING FROM CONTAMINATING A STERILE ENVIRONMENT," the entire contents of which are hereby incorporated by reference into this disclosure as if set forth fully herein.

FIELD OF THE INVENTION

The present disclosure is directed to a method and apparatus for reducing the occurrence of bacterial contamination resulting from the use of unclean personal items in a workplace.

BACKGROUND

Millions of surgical procedures are undertaken each year across the United States. While most surgical procedures are completed without incident, complications do arise. Surgical site infections are the third-most common hospital-acquired infection. These infections often result in longer hospital stays and increased costs to the patient and hospital. To ensure each patient undergoing a surgical procedure does not suffer from surgically related infection and to prevent the spread of pathogens, aseptic techniques are employed. As such, aseptic techniques and procedures are vital to reducing morbidity and mortality associated with hospital infections. Aseptic techniques are employed in any clinical setting in order to maximize and maintain a room free of pathogenic organisms. A pathogen-free environment is critical as pathogens can introduce infection to patients through non-sterile environments, personnel, and/or surgical or non-surgical equipment.

Surgical procedures within an operating room require the strictest adherence to aseptic techniques. It is within this setting that a patient is often most vulnerable, as the patient requires opening body cavities to fix diseased internal organs or tissues or to fix open wounds. Typical aseptic techniques involve preparing and cleaning the surgical site, possible clipping of hair, applying a disinfectant solution to the area, and using sterile surgical draping. In addition, all surgical staff that enters an operating room undergoes surgical scrubbing and is clothed in sterile surgical gowns. The use of sterile gloves, masks, and goggles are used as barriers against pathogens. Finally, it is of vital importance that all surgical instruments and/or equipment used in the procedure are properly sterilized.

Improper aseptic techniques can result in various surgery-related complications for the patient, including death. Avoiding such surgical complications often depends on whether all aseptic techniques were properly followed. In addition, it is vital that all members involved in the surgical procedure properly follow the aseptic techniques. While the surgeons performing the procedure may have followed proper procedures, the patient may be compromised if even one of the staff has not done so.

Personal mobile communication devices, for example cellular telephones ("cell phones"), data-enabled cellular telephones ("smart phones"), and tablet computers ("tablets") have become ubiquitous in society at large and have effectively replaced the pager as the primary means of communication in the medical field. While the technological advancements in communication devices provide immense benefits to everyone including the medical community, one pitfall of these devices that most people seem to be unaware of is that cell phones are exceptional reservoirs for bacteria, including dangerous pathogens. The main reason for this is simply because users do not clean their phones regularly, if at all. People also commonly use their phones during and after meals without washing their hands, during bathroom visits, after playing with pets, on public transportation, etc. The result is that most peoples' cell phones are dirtier (in terms of germs per square inch) than public toilets, kitchen counters, shoe soles, and doorknobs.

While most surgical staff, surgical supplies, and surgical equipment are properly sterilized, other objects such as personal items may be unwittingly brought into a sterile environment, contaminating the area. Personal mobile communication devices are examples of common personal items that are often brought into the sterile operating room environment. Cell phone usage is a vital means of communication and usage is extensive. In addition to receiving and making calls, most smart cell phones allow individuals to connect to others using various communication platforms such as email, text messaging, TWITTER, FACEBOOK, or other social media platforms. Smart phones also provide access to various sources of information, such as the Internet. Because of their widespread and constant use, unclean cell phones can be a major source of unwelcome bacteria introduced into an otherwise sterile environment. As a result, it is entirely possible that the use of cell phones in the operating room is a major cause of surgical site infections.

One example of a typical situation in which a contaminated cell phone is introduced into a sterile environment involves a scenario in which a surgeon or surgical staff leaves the sterile operating room in order to use the bathroom. Often times this is the only time that the doctor or surgical staff can contact individuals outside of the operating room environment. This is especially true if a surgical procedure is lengthy. Once the surgeon or surgical staff finishes using the phone in the bathroom, they often place it back into the pocket of their surgical attire. While they wash their hands before leaving the bathroom and even rescrub back into the surgical environment, the cell phone is almost never properly cleaned and thus is most likely contaminated with bacteria. Once the non-sterile cell phone enters the sterile surgical environment, it has the potential to be a major source of bacterial contamination within the surgical environment. Additionally, since text messages have replaced pagers for many surgeons, it is not uncommon for circulating nurses and/or other operating room personnel to pick up a surgeon's cell phone to read the text messages to the surgeon (who is scrubbed) and respond at the surgeon's direction in order to triage patient care, answer questions, etc. As such, any germs on the phone may be transferred to multiple users and quickly spread to many people in the otherwise sterile operating room.

SUMMARY

The present disclosure is directed to a method and apparatus for reducing the occurrence of bacterial contamination resulting from the use of unclean personal items in a bacterially sensitive environment. By way of illustrative example, the features and advantages will be described herein throughout in relation to the use of cell phones by surgeons (and other hospital staff) in an operating room environment. However, it should be noted that the advantages and benefits of sanitizing a cell phone are applicable in a wide array of situations where a) an employee would like to have their phone protected from their work environment or b) the user works in a place where, not unlike the operating room, introducing bacteria from one's phone into the work environment would be undesirable. Some examples include other medical services (e.g. dentist, routine doctor visits, anywhere else in a hospital, etc), industrial applications (e.g. meat processing and packing, FDA inspected facilities, USDA inspected facilities, tire plants etc), retail services (e.g. food preparation), and public services (e.g. mass transit, school, etc). Additionally, the cell phone sanitization apparatus and method may be provided in a more compact version for personal use, for example in one's home, office, or car.

Generally, the method for reducing the occurrence of bacterial contamination resulting from the use of unclean personal items in a bacterially sensitive environment disclosed herein involves the use of a sanitization apparatus, an example of which is also disclosed herein. Typically, the sanitization apparatus would be positioned adjacent an entry into the bacterially sensitive environment so as to ensure that the user follows the sanitization method immediately prior to entering the bacterially sensitive environment. The sanitization apparatus may be wall-mounted, and in some instances may extend through the wall so that the user deposits an unclean personal item outside the bacterially sensitive environment and then retrieves the sanitized personal item within the bacterially sensitive environment. The first step of the method is to insert a user's personal item into the sanitization apparatus. The user then selects the desired sanitization method, if multiple options are available. Preferably, the sanitization apparatus includes at least three different sanitization options (e.g. ultraviolet radiation, sealing the personal item in a clear container, and shrink wrapping the personal item with transparent film). While the user's personal item is being sanitized, the user may sanitize his/her hands using hand sanitizer solution dispensed from a hand sanitizer solution dispenser, which may by attached to the sanitization apparatus. When the personal item has been sanitized, it is released into a retrieval reservoir where the user may remove the now sanitized personal item from the sanitization apparatus. Optionally, the sanitization apparatus may be configured to require the dispensing of hand sanitizer solution prior to release of the sanitized personal item into the retrieval reservoir.

By way of example, the sanitization apparatus described herein includes a receiving slot, a dispensing reservoir, a hand sanitizing solution dispenser, and a selection interface. Once the personal item (e.g. cell phone) is inserted into the sanitization apparatus through the receiving slot, the user selects the manner of sanitization using the selection interface. The selection interface may take any form that allows for user-driven selection of the sanitization manner, including but not limited to a plurality of buttons, a LED touch screen interface where the user simply selects the desired sanitization by touching a selection on a graphic user interface display, and the like.

If UV radiation is the selected manner of sanitization, the personal item is exposed to UV radiation within a UV radiation compartment, for example ultraviolet germicidal radiation (UV-C) for a period of time sufficient to kill pathogens.

If the clear plastic container option is selected, the personal item is transferred to the clear container sanitization compartment, where the dirty personal item is sealed within a single-use, non-resealable clean (or sterile) clear plastic container. The specific container is shown and described by way of example as a clear plastic bag, however other clear containers may be possible. The plastic material is such that allows a user to operate the personal item through the plastic barrier in the manner intended while potentially wearing surgical gloves (e.g. latex or otherwise). The personal item is placed into a clean (or sterile) clear bag through an open end of the bag. Once the personal item is placed inside the bag, the bag is sealed using any manner for sealing plastic bags, for example a heat sealing source.

If the transparent plastic film option is selected, the personal item is transferred to the transparent plastic film sanitization compartment, where the dirty personal item is encapsulated (e.g. by shrink-wrapping) in a transparent plastic film. As with the plastic container (bag), the plastic film material is such that allows a user to operate the personal item in the manner intended through the plastic barrier while potentially wearing surgical gloves (e.g. latex or otherwise). Using a heat source to apply heat to the transparent and translucent heat shrink plastic material shrink-fits the clear plastic wrap to the personal item, thereby encasing the personal item with a sanitized (or sterile) protective covering.

To ensure that the personal item remains sanitized prior to entry into a bacterially sensitive environment, the sanitization apparatus may include a hand sanitizing solution dispenser attached to the side (by way of example) thereof. Optionally, the sanitization apparatus may be programmed to dispense the sanitized personal item only after hand-sanitizing solution has been dispensed through the hand sanitizing solution dispenser. This would ensure that the sanitized personal item is not touched by dirty hands, as this could compromise the clean status of the sanitized personal item.

According to one broad aspect of the disclosure, a sanitization apparatus configured to sanitize a user's personal object to prevent bacterial cross-contamination between a user's personal object and a bacterially sensitive environment is described. The sanitization apparatus comprises an object sanitizer unit including a object ingress aperture for receiving a user's object therethrough, at least one object sanitization compartment, an object retrieval reservoir, a hatch door forming at least part of the barrier between the at least one object sanitization compartment and the object retrieval reservoir, and a programmable control unit in electronic communication with the at least one object sanitization compartment and hatch door, the control unit programmable to open the hatch door after the user's personal object has been sanitized in the object sanitization compartment The object sanitizer unit is configured to receive an unsanitized object through the object ingress aperture, transform the object from an unsanitized object to a sanitized object in the object sanitization compartment, and thereafter eject the sanitized object into the object retrieval reservoir.

Various additional features and functions form aspects of the aforementioned apparatus of this disclosure, including not limited to one or more of the following: The at least one object sanitization compartment may comprise at least one of an ultraviolet radiation compartment, a clear container sanitization compartment, and a clear film sanitization compartment. The ultraviolet radiation compartment may include at least one ultraviolet radiation emitter. The ejected sanitized object may comprise the user's object after exposure to ultraviolet radiation. The clear container sanitization compartment may include an open clear container and a sealing element. The open clear container may be sterile. The clear container may comprise a single-use, non-resealable, transparent plastic bag. The ejected sanitized object may comprise the user's object sealed within the single-use, non-resealable, transparent plastic bag. The film sanitization compartment may include a roll of transparent plastic film and a heating element. The transparent plastic film may sterile. The ejected sanitized object may comprise the user's object tightly encapsulated by a transparent plastic film that has been shrink-wrapped about the object using the heating element. The at least one object sanitization compartment may comprise at least three object sanitization compartments, the at least three object sanitization compartments including an ultraviolet radiation compartment, a clear container sanitization compartment, and a transparent film sanitization compartment. The sanitization apparatus may further comprise a selection interface in electronic communication with the control unit, the selection interface including a user-operated selection mechanism that enables the user to select the sanitization option. The sanitization apparatus may further comprise a hand sanitizer solution dispenser attached to the outside of the object sanitizer unit. The hand sanitizer solution dispenser may be in electronic communication with the programmable control unit. The control unit may be programmable to open the hatch door only after hand sanitizer solution has been dispensed from the hand sanitizer solution dispenser. The object may be a handheld mobile communication device.

According to another broad aspect of the disclosure, a method of preventing bacterial cross-contamination between a user's personal item and a bacterially sensitive environment is described. The method includes the following steps: (1) sealing the personal item within a single-use, non-resealable airtight container immediately prior to entering the bacterially sensitive environment, at least a portion of the airtight container comprising a transparent film that enables the user to use the personal item as intended while sealed within the airtight container; (2) extracting the personal item from the single-use, non-resealable airtight container after exiting the bacterially sensitive environment; and (3) disposing of the single-use, non-resealable airtight container.

Various additional features and functions form aspects of the aforementioned method of this disclosure, including not limited to one or more of the following: The bacterially sensitive environment may be an surgical environment. The method may comprise the further step of sterilizing the single-use, non-resealable airtight container. The step of sterilizing the single-use, non-resealable airtight container may comprise exposing the single-use, non-resealable airtight container to ultraviolet radiation for a predetermined period of time. The single-use, non-resealable airtight container may comprise a transparent plastic bag. The single-use, non-resealable airtight container may comprise a transparent plastic film. The method of may comprise the further steps of: encapsulating the personal item within a portion of the transparent plastic film; and using a heating element to apply heat to the transparent plastic film to create a shrink wrap seal of transparent plastic film about the personal item. The personal item may be a mobile communication device. The mobile communication device may be one of a cellular telephone, smart phone, and tablet computer. The method may comprise the further step of sanitizing the user's hands by applying a hand sanitizer solution to the user's hands prior to handling the sealed airtight container containing the user's personal item.

According to another aspect of the disclosure, a method of contemporaneously sanitizing a user's object and hands is described. The method comprises the steps of: (1) providing a multi-functional sanitization apparatus configured to separately and contemporaneously sanitize an object and a user's hands, the multi-functional sanitization apparatus comprising a housing unit and a hand sanitizer solution dispenser attached to the outside of the housing unit, the housing unit including a receiving aperture for receiving a user's object therein, at least one object sanitization compartment, and an object retrieval reservoir; (2) inserting a non-sterile object into the receiving aperture; (3) initiating a sanitization protocol for the non-sterile object, whereby the object is transferred into one of the at least one sanitization compartment; (4) using a volume of hand sanitizer solution dispensed from the hand sanitizer solution dispenser to sanitize the user's hands while the sanitization apparatus is sanitizing the non-sterile object within the selected sanitization compartment and thereby converting the non-sterile object to a sanitized object; and (5) retrieving the sanitized object from the object retrieval reservoir.

Various additional features and functions form aspects of the aforementioned method of this disclosure, including not limited to one or more of the following: The at least one object sanitization compartment may comprise at least one of an ultraviolet radiation compartment, a clear sterile bag sanitization compartment, and a clear sterile film sanitization compartment. The object may be a handheld personal communication device.

Other objectives and advantages of this disclosure will become apparent from the following description taken in conjunction with any accompanying drawings wherein are set forth, by way of illustration and example, certain embodiments of this disclosure. Any drawings contained herein constitute a part of this specification and include example embodiments of the present disclosure and illustrate various objects and features thereof.

BRIEF DESCRIPTION OF THE DRAWINGS

FIG. 7 is a perspective view of a clear film sanitizer component forming part of the sanitization apparatus of FIG. 2, illustrating in particular an example of a personal object (e.g. cell phone) positioned for encapsulation by a sterile clear film;

FIG. 8 is a perspective view of the clear film sanitizer component of FIG. 7, illustrating in particular the film positioned around the personal object prior to heat sealing;

FIG. 9 is a perspective view of the clear film sanitizer component of FIG. 7, illustrating in particular the film being heat sealed around the personal object.

DETAILED DESCRIPTION OF THE PREFERRED EMBODIMENTS

Figure 1:
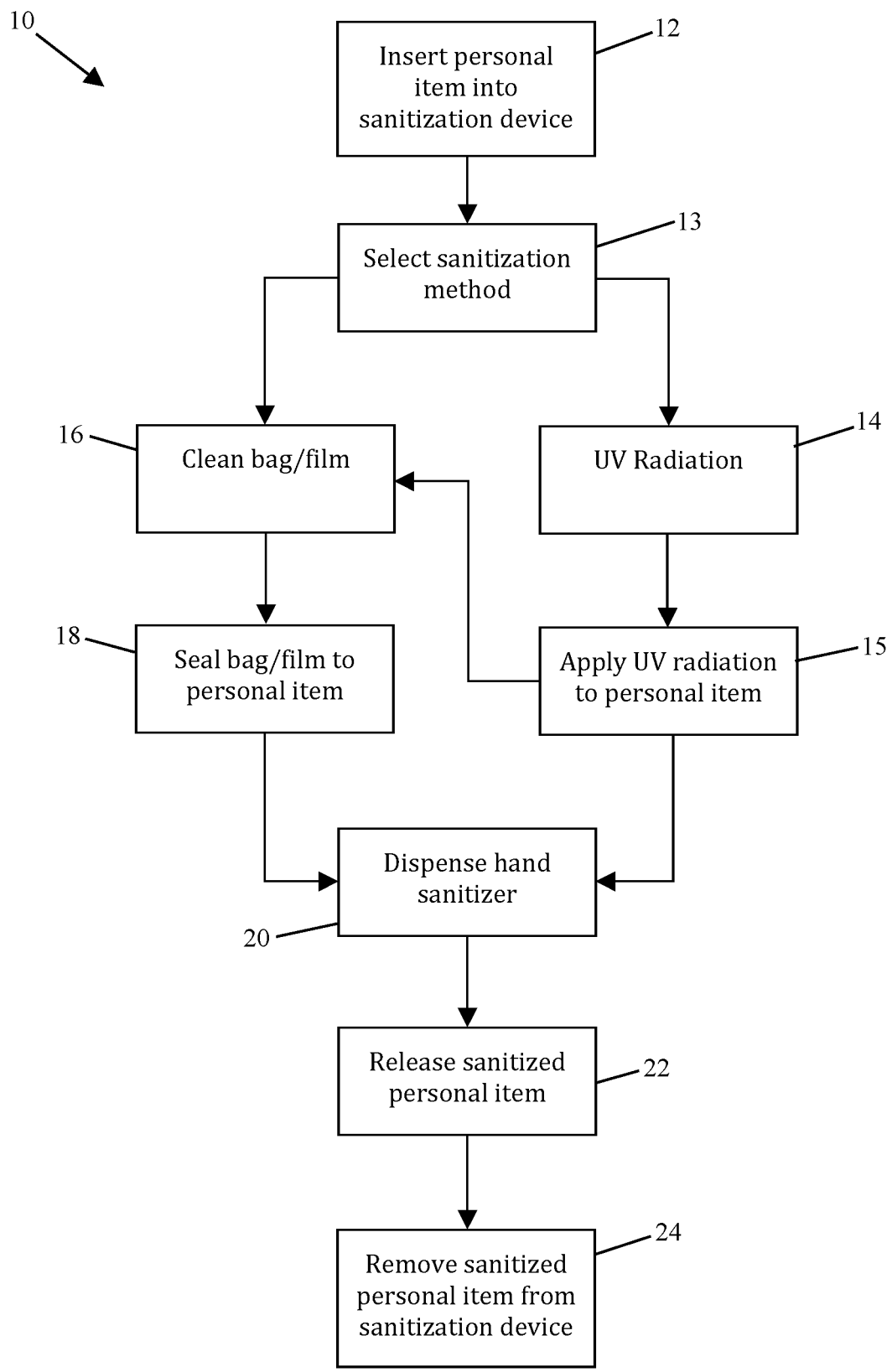
FIG. 1 is a flow chart depicting the various steps of one example of a method for reducing the occurrence of bacterial contamination resulting from the use of unclean personal items in a bacterially sensitive environment, according to one embodiment of the disclosure.

While the method and apparatus described herein is susceptible of embodiment in various forms, there is shown in the drawings and will hereinafter be described a presently preferred, albeit not limiting, embodiment with the understanding that the present disclosure is to be considered an exemplification only and is not intended to be limited to the specific embodiments illustrated.

The present disclosure is directed to a method and apparatus for reducing the occurrence of bacterial contamination resulting from the use of unclean personal items in a workplace. By way of example, the method and apparatus are described herein in terms of ensuring that handheld mobile communication devices (e.g. cell phones, smart phones, tablets, and the like) brought into a sterile operating room will be sanitized prior to entry. Despite surgeons and surgical staff covering their feet and head to prevent the transmission of bacteria, many bring in and use their cell phones without ensuring that it will not contaminate the sterile environment. As such, the method described herein begins prior to any personnel entering into a surgical room.

FIG. 1 provides a flowchart illustrating a general outline of the method, referred to generally as the method of reducing the occurrence of bacterial contamination resulting from the use of unclean personal items in a bacterially sensitive environment 10 (such as an operating room), or method 10. The first step 12 is to insert a user's personal item into the sanitization device. In the operating room ("OR") example, this means that immediately prior to entering into any sterile area (e.g. OR), the surgeon (and/or surgical staff etc.) inserts any personal item that has not been previously (immediately) sanitized into a device that converts the unsanitized (or "dirty") item into a sanitized (or "clean") item. For illustrative purposes, the personal item that has not been previously sanitized is described herein throughout as a cell phone (mobile phone or smart phone can be used interchangeably), however it should be understood that the method and apparatus described herein is not limited to cell phones or mobile handheld communication devices, but rather can be used to sanitize any variety of personal items whether or not mentioned specifically in this disclosure.

Figure 2:
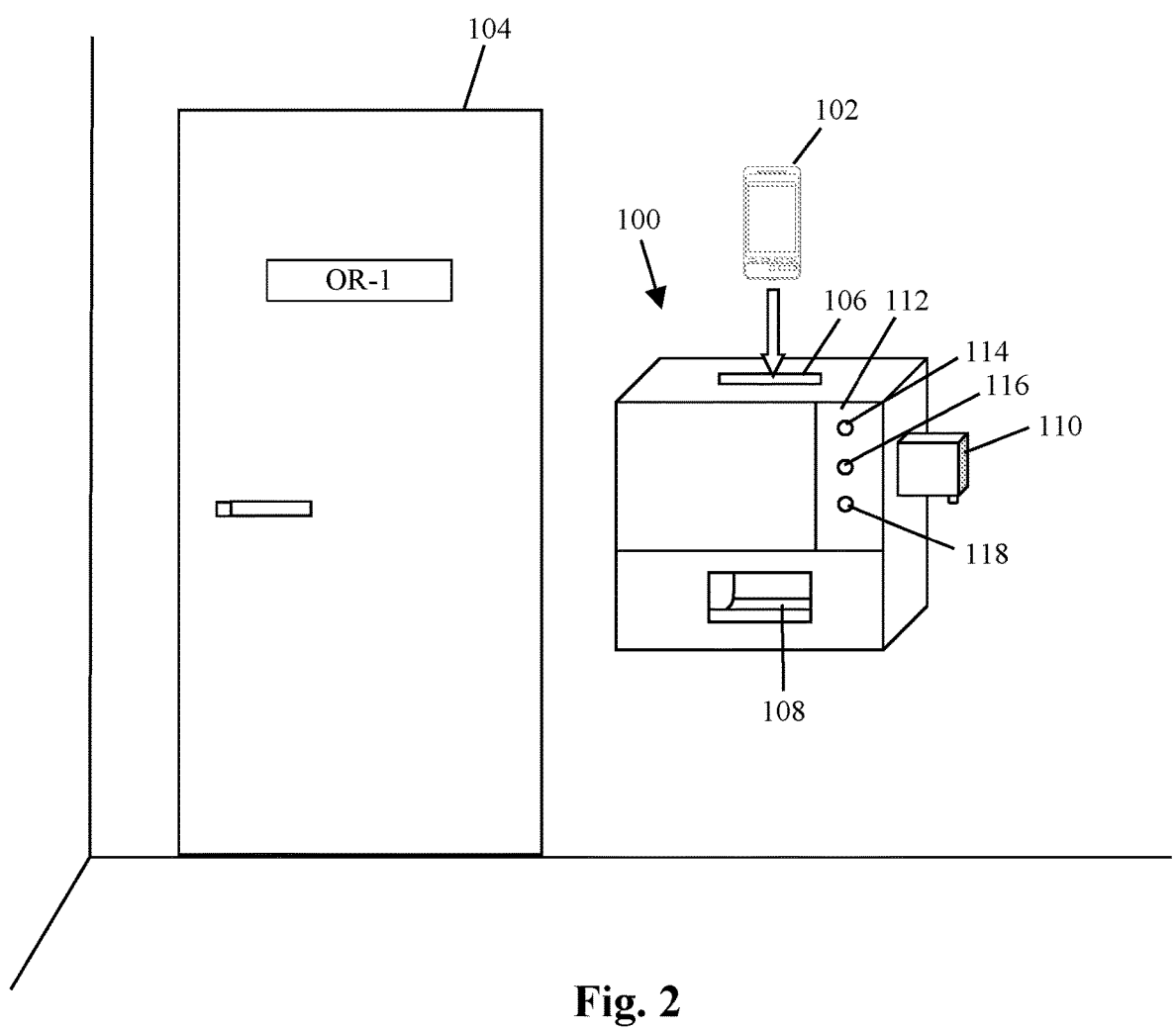
FIG. 2 is a perspective view of an example of a sanitization apparatus according to one embodiment of the disclosure, positioned outside of a hospital operating room.

FIG. 2 illustrates an example of a sanitization apparatus 100 capable of sanitizing a user's cell phone 102 and hands prior to entry into the operating room to help reduce the occurrence of contaminating the sterile OR environment, according to one aspect of the disclosure. By way of example, the sanitization apparatus 100 is preferably positioned adjacent the entrance 104 (e.g. door) of a surgical room and may be wall-mounted (as shown) or provided on a stand, cart, table, etc. Optionally, the sanitization apparatus 100 may extend through the wall such that the user inserts a dirty cell phone into the sanitization apparatus 100 in the hallway and retrieves the sanitized cell phone inside the sterile OR. The sanitization apparatus 100 includes a receiving slot 106, a dispensing reservoir 108, a hand sanitizing solution dispenser 110, and a selection interface 112, the details of which will be discussed further below. To satisfy the first step 12 of the method 10, the surgical staff (or anyone entering the sterile environment) would be required to remove their cell phone 102 (or other personal item) and place it into the receiving slot 106 prior to entry through door 108 of the surgical room 102.

Referring now to FIGS. 1 and 2, to satisfy the next step 13 of the method 10, the user then selects the manner in which the cell phone 102 becomes sanitized. In the illustrative example, the cell phone 102 can be sanitized by either exposing the cell phone 102 to UV radiation (step 14) and/or by enclosing the cell phone 102 in a clean, clear container or a clean, clear film (step 16). Once the cell phone 102 is inserted into the sanitization apparatus 100 through slot 106, the user selects the manner of sanitization using the selection interface 112. By way of example, only, the selection interface 112 illustrated herein includes a plurality of selection buttons that correspond to a particular manner of sanitization, for example a UV radiation button 114, container sanitization button 116, or film wrap sanitization button 118. While the selection interface 112 is shown herein with buttons, the selection interface 112 may take any form that allows for user-driven selection of the sanitization manner, including but not limited to a LED touch screen interface where the user simply selects the desired sanitization by touching a selection on a graphic user interface display.

Figure 3:
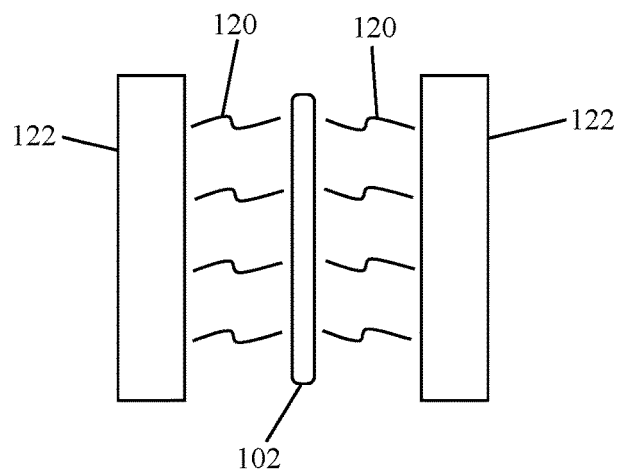
FIG. 3 is a plan view of an ultraviolet (UV) radiation sanitizer component forming part of the sanitization apparatus of FIG. 2.

Once inserted into the sanitization apparatus 100, the cell phone 102 can be sanitized in several ways. One manner of sanitization can be achieved by using a UV radiation (step 14). In this process, the cell phone 102 is exposed to UV radiation, for example ultraviolet germicidal radiation (UV-C) for a period of time sufficient to kill pathogens (step 15). By way of example, FIG. 3 illustrates the cell phone 102 being exposed to UV-C radiation 120 produced by one or more UV radiation emitters 122. Since sanitization by UV-C radiation is based on direct exposure to radiation waves, it is preferable to use at least two emitters, with one emitter positioned on either side of the personal item. Any type of UV-C technique may be used, including but not necessarily limited to LED and mercury vapor. Once the cell phone is exposed to the UV radiation 120, it is ready to be dispensed back to the user via the dispensing reservoir 108 (FIG. 2). However, if so desired the user can direct the sanitization apparatus to also seal the UV-sanitized cell phone 102 within a clear plastic bag or film before dispensing the cell phone 102.

Figure 4:
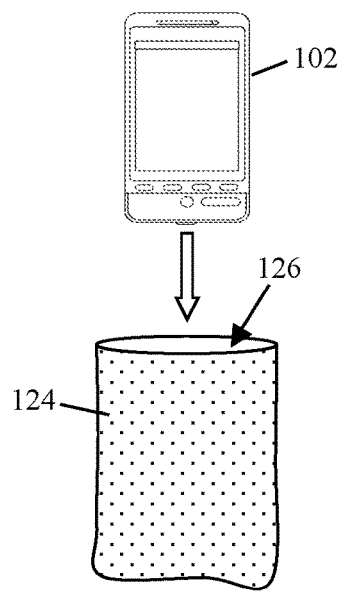
FIG. 4 is a perspective view of a clear container sanitizer component forming part of the sanitization apparatus of FIG. 2, illustrating in particular an example of a personal object (e.g. cell phone) positioned for insertion into a clear bag.
Figure 5:
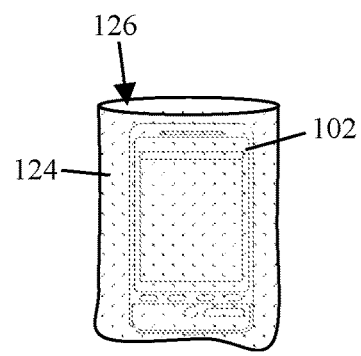
FIG. 5 is a perspective view of the clear container sanitizer component of FIG. 4, illustrating in particular the insertion of the personal object into the clear bag.
Figure 6:
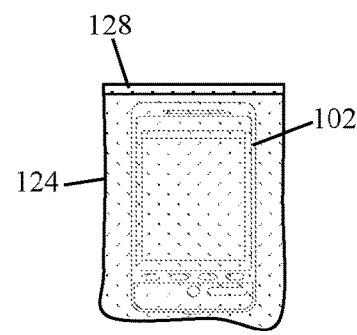
FIG. 6 is a perspective view of the clear container sanitizer component of FIG. 4, illustrating in particular the sealed clear bag encapsulating the personal object.

An alternative sanitizing manner includes sealing the dirty cell phone 102 within a clean (or sterile) clear plastic container or film (FIG. 1, step 18). FIGS. 4-6 illustrate the process of sealing the dirty cell phone 102 within a clean (or sterile), clear plastic container 124. The specific container 124 is shown and described by way of example as a clear plastic bag 124, however other clear containers may be possible without departing from the scope of the disclosure, including but not limited to a soft-walled shell casing, clear box, and the like. Because the current cell phone/smart phone technology incorporates a sensitive touch screen, the plastic material is such that allows a user to operate the cell phone through the plastic barrier while potentially wearing surgical gloves (e.g. latex or otherwise). The plastic material may also have anti-microbial properties to help prolong the sanitized state of the cell phone 102. The cell phone 102 (is placed into a clean (or sterile) clear bag 124 through an open end 126 of the bag 124. Once the cell phone 102 is placed inside the bag 124, the bag 124 is sealed, using any manner for sealing plastic bags, for example a heat sealing source (which creates a seal line 128). Sealing the cell phone 102 within the clean, clear plastic bag 124 allows the cell phone 102 to be taken into the operating room without the risk of spreading pathogens as the cell phone 102 is now in a sanitized condition. The sanitized condition allows an individual to use the cell phone 102 inside the operating room regardless of how dirty the cell phone may be inside the container 124.

FIGS. 7-9 illustrate the process of sealing the cell phone 102 within a clean (or sterile), clear plastic film 130, such as a transparent and translucent heat shrink plastic material. Examples if suitable materials include, but are not limited to, polyethylene terephthalate (PET), PET-G, orientated polystyrene (OPS), polylactic acid (PLA) films, or any combinations thereof. As with the plastic container (bag) 124 described above, the plastic film material is such that allows a user to operate the cell phone through the plastic barrier while potentially wearing surgical gloves (e.g. latex or otherwise). The plastic film material may also have antimicrobial properties to help prolong the sanitized state of the cell phone 102. Using a heat source 132 to apply heat 134 to the transparent and translucent heat shrink plastic material shrink-fits the clear plastic wrap 130 to the cell phone 102, thereby encasing the cell phone 102 with a sanitized (or sterile) protective covering. Encasing the cell phone 102 within the clear plastic film 130 allows the cell phone 102 to be taken into the operating room without the risk of spreading pathogens as the cell phone 102 is now in a sanitized condition. The sanitized condition allows an individual to use the cell phone 102 inside the operating room.

Referring again to FIGS. 1 and 2, to ensure that the cell phone 102 remains sanitized prior to entry into a sterile environment, the sanitization apparatus 100 may include a hand sanitizing solution dispenser 110. The hand sanitizing solution dispenser 110 is attached to the side (by way of example) of the sanitization apparatus 100 and dispenses a hand sanitizing solution, e.g. including but not limited to alcohols such as ethanol and/or isopropanol, sometimes combined with quats (quaternary ammonium cations) such as benzalkonium chloride. Optionally, the sanitization apparatus may be programmed to dispense the sanitized cell phone 102 only after hand-sanitizing solution has been dispensed through the hand sanitizing solution dispenser 110. This would ensure that the sanitized cell phone 102 is not touched by dirty hands, as this could compromise the clean status of the sanitized cell phone 102. Thus, after the cell phone 102 has been sanitized, the next step 20 in the method 10 is to dispense hand sanitizer. This may be accomplished by any suitable mechanism (not shown), for example including a user-operated lever, button, or motion sensing device. Optionally, the hand sanitizing solution may be dispensed automatically, for example after a predetermined time has elapsed after insertion of the cell phone 102 into the receiving slot 106. Additionally, the sanitization apparatus 100 may be adapted work in concert with an existing hand sanitizer dispenser (as opposed to attached dispenser 110) to detect whether the existing hand sanitizer dispenser has dispensed sanitizer to the user. The sanitization apparatus 100 may be configured such that the dispensing of the hand sanitizing solution through the hand sanitizing solution dispenser 110 allows the next step 22 of the method 10 to be performed, which is the releasing of the sanitized personal item (cell phone 102 in this case) into the dispensing reservoir 108. The final step 24 of the method 10 is the removal of the sanitized personal item (cell phone 102) from the dispensing reservoir 108.

The method 10 described above pertains to the sanitization on one's cell phone (or other personal item) and hands prior to entering a sterile operating room (for example). It should be noted that if a user were to leave the operating room and reenter (or enter a different sterile area), the user would have to remove the container 124 or film 130 (if used) and repeat the process upon reentry into a sterile room. This is because once one leaves the sterile room there are no guarantees that their phone (even in the sanitization package) and/or hands will remain sterile. In that regard, the receiving slot 106 may be configured to not accept a cell phone (or other personal item) that already has a sanitization bag or wrap on it.

Figure 10:
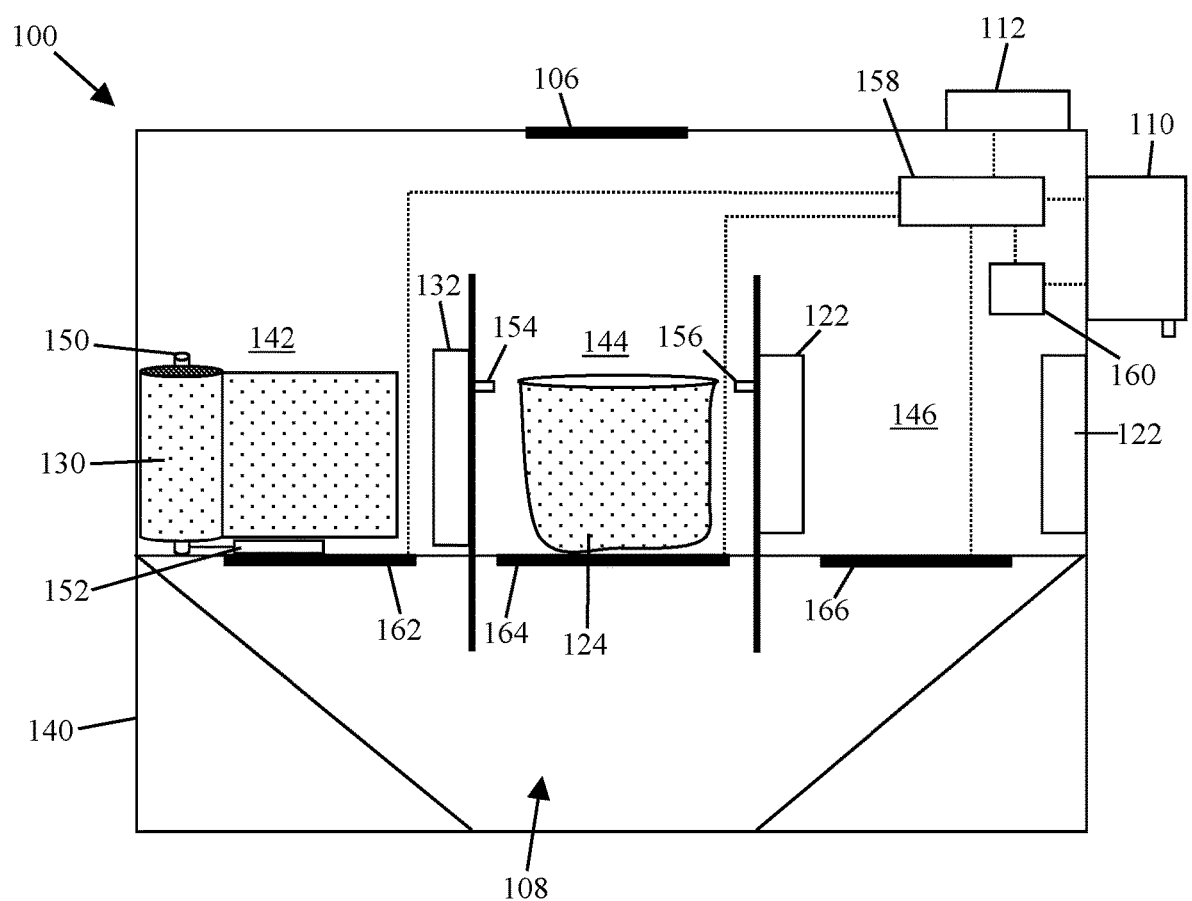
FIG. 10 is a block diagram illustrating the interior components of the sanitization apparatus of FIG. 2.

FIG. 10 is a block diagram showing an illustrative example of the internal components of a sanitization apparatus 100 having all three sanitization manners described herein. A housing unit 140 stores all the internal components. As the user inserts the cell phone 102 into the slot 106, the cell phone 102 is directed to one of three compartments, a clear plastic material compartment 142, a plastic container compartment 144, and a UV radiation compartment 146. Which compartment 142, 144, or 146 the cell phone is directed to depends upon which sanitization technique is requested via interaction with the selection interface 112. The clear plastic material compartment 142 contains a spool 150 with clear plastic material 130. The clear plastic material 130 may be clear or sterile. A motor 152 is operatively coupled to the spool 150 to allow for the clear plastic material 130 to be applied to the cell phone 102. The heat source 132 provides a mechanism for the clear plastic material 130 to shrink fit onto the cell phone 102. The heat source 132 may also be used to release the sealed phone 102 from the spool 150.

The plastic container compartment 144 contains an open plastic bag 124 (by way of example), a cutting mechanism 154, and a sealing mechanism 156. The UV radiation compartment 146 contains a plurality of UV radiation emitters 122. A control unit 158 and power source 160 are operatively coupled to the one or more components to drive each component's functionality. The hand sanitizing solution dispenser 110 may be operatively coupled to the control unit 158 to 1) automatically dispense the sanitizing solution (optionally), and/or 2) to communicate to the control unit 158 that hand sanitizing solution has been dispensed, which in turn allows a clear plastic material compartment door 162, a plastic bag compartment door 164, or a UV radiation compartment door 166 to open. This allows the sanitized cell phone 102 to be dispensed into the dispensing reservoir 108 where a user can then obtain possession of a sanitized cell phone 102. The sanitized cell phone 102 is now free to use and should not be responsible for introducing pathogens into the sterile environment.

Although shown and described herein by way of example only for use in a sterile surgical medical environment, it is worth repeating that cell phones are exceptional reservoirs for bacteria and most people would likely be alarmed at exactly how much their cell phone is contaminated with pathogenic bacteria. Accordingly, it should be understood that the advantages and benefits of sanitizing a cell phone and user's hands are applicable in a wide array of situations where a) an employee would like to have their phone protected from their work environment or b) the user works in a place where, not unlike the operating room, cross-contamination would be undesirable. Some examples include outpatient medical services (e.g. dentist, routine doctor visits, etc), industrial applications (e.g. meat processing and packing, FDA inspected facilities, USDA inspected facilities, tire plants etc), retail services (e.g. food preparation), and public services (e.g. mass transit, school, etc). Additionally, the sanitization apparatus 100 may be provided in a more compact version for personal use, for example in one's home, office, or car.

Sealing a cell phone in a plastic bag (or shrink wrap) has further benefits other than the stated goal of preventing pathogenic bacteria from being transferred from the phone to a work environment (or vice versa, depending on the work environment). More specifically, a sealed plastic bag (or shrink wrap) as provided by the sanitization apparatus 10 would be at least temporarily (depending on how a user treats their phone) protected from certain environmental phone hazards, including but not limited to dirt and water. So while the plastic barrier would not provide much protection from forcible impact, it could enhance the protection provided by most phone protectors currently on the market by keeping dirt and water out.

It is to be understood that while a specific embodiment of the invention is illustrated by way of example, it is not to be limited to the specific form or arrangement shown and described herein. It will be apparent to those skilled in the art that various changes may be made without departing from the scope of the invention and the invention is not to be considered limited to what is shown and described in the specification and any drawings/figures included herewith.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A sanitization apparatus configured to sanitize a user's personal object to prevent bacterial cross-contamination between a user's personal object and a bacterially sensitive environment, comprising:
    an object sanitizer unit including an object ingress aperture for receiving a user's object therethrough, at least three object sanitization compartments, an object retrieval reservoir, and a hatch door forming at least part of the barrier between the at least three object sanitization compartments and the object retrieval reservoir, wherein the at least three object sanitization compartments comprise an ultraviolet radiation compartment, a clear container sanitization compartment, and a clear film sanitization compartment;
    a programmable control unit in electronic communication with the at least one object sanitization compartment and hatch door, the control unit programmable to open the hatch door after the user's personal object has been sanitized in at least one of the at least three object sanitization compartments;
    a selection interface in electronic communication with the control unit, the selection interface including a user-operated selection mechanism having at least three different selectable sanitization options corresponding to the at least three sanitization compartments that enables the user to select the sanitization compartment; and
    a hand sanitizer solution dispenser attached to an outside portion of the object sanitizer unit;
    wherein the object sanitizer unit is configured to receive an unsanitized object through the object ingress aperture, transform the object from an unsanitized object to a sanitized object in at least one of the at least three object sanitization compartments, and thereafter eject the sanitized object into the object retrieval reservoir, and
    wherein the hand sanitizer solution dispenser is in electronic communication with the programmable control unit, and the programmable control unit is programmable to open the hatch door only after hand sanitizer solution has been dispensed from the hand sanitizer solution dispenser.

2. The sanitization apparatus of claim 1, wherein the ultraviolet radiation compartment includes at least one ultraviolet radiation emitter.

3. The sanitization apparatus of claim 2, wherein the ejected sanitized object comprises the user's object after exposure to ultraviolet radiation.

4. The sanitization apparatus of claim 1, wherein the clear container sanitization compartment includes an open clear container and a sealing element.

5. The sanitization apparatus of claim 4, wherein the open clear container is sterile.

6. The sanitization apparatus of claim 4, wherein the clear container comprises a single-use, non-resealable, transparent plastic bag.

7. The sanitization apparatus of claim 6, wherein the ejected sanitized object comprises the user's object sealed within the single-use, non-resealable, transparent plastic bag.

8. The sanitization apparatus of claim 1, wherein the clear film sanitization compartment includes a roll of transparent plastic film and a heating element.

9. The sanitization apparatus of claim 8, wherein the transparent plastic film is sterile.

10. The sanitization apparatus of claim 8, wherein the ejected sanitized object comprises the user's object tightly encapsulated by the transparent plastic film that has been shrink-wrapped about the object using the heating element.

11. The sanitization apparatus of claim 1, wherein the object is a handheld mobile communication device.

* * * * *